(12) United States Patent
Lakare et al.

(10) Patent No.: US 8,447,081 B2
(45) Date of Patent: May 21, 2013

(54) PULMONARY EMBOLI DETECTION WITH DYNAMIC CONFIGURATION BASED ON BLOOD CONTRAST LEVEL

(75) Inventors: Sarang Lakare, Maharashtra (IN); Dinesh Mysore Siddu, Bangalore (IN)

(73) Assignees: Siemens Medical Solutions USA, Inc., Malvern, PA (US); Siemens Information Systems, Ltd., Bangalore (IN)

( * ) Notice: Subject to any disclaimer, the term of this patent is extended or adjusted under 35 U.S.C. 154(b) by 773 days.

(21) Appl. No.: 12/578,768

(22) Filed: Oct. 14, 2009

(65) Prior Publication Data

US 2010/0098308 A1 Apr. 22, 2010

Related U.S. Application Data

(60) Provisional application No. 61/105,945, filed on Oct. 16, 2008.

(51) Int. Cl.
*G06K 9/00* (2006.01)

(52) U.S. Cl.
USPC .......................................... 382/128

(58) Field of Classification Search
USPC .......................................... 382/128
See application file for complete search history.

(56) References Cited

U.S. PATENT DOCUMENTS

| | | | |
|---|---|---|---|
| 7,203,353 B2* | 4/2007 | Klotz et al. | 382/131 |
| 2005/0207630 A1* | 9/2005 | Chan et al. | 382/131 |
| 2008/0015419 A1* | 1/2008 | Summers et al. | 600/300 |
| 2009/0012382 A1* | 1/2009 | Dutta et al. | 600/407 |
| 2009/0052763 A1* | 2/2009 | Acharyya et al. | 382/132 |
| 2009/0097730 A1* | 4/2009 | Kasai et al. | 382/132 |

* cited by examiner

*Primary Examiner* — Gerald J. O'Connor
*Assistant Examiner* — Trang Nguyen
(74) *Attorney, Agent, or Firm* — Peter R. Withstandley

(57) ABSTRACT

A method for automatically detecting pulmonary embolism (PE) candidates within medical image data using an image processing device includes administering radiocontrast into a patient. A sequence of computed tomography (CT) images is acquired. A level of radiocontrast at a pulmonary artery trunk of the patient is determined. One or more PE candidates are detected within a pulmonary artery tree of the patient based on the determined level of radiocontrast at the pulmonary artery trunk. The one or more detected PE candidates are displayed.

12 Claims, 4 Drawing Sheets

PULMONARY EMBOLI DETECTION WITH DYNAMIC CONFIGURATION BASED ON BLOOD CONTRAST LEVEL

CROSS-REFERENCE TO RELATED APPLICATION

The present application is based on provisional application Ser. No. 61/105,945, filed Oct. 16, 2008, the entire contents of which are herein incorporated by reference.

BACKGROUND OF THE INVENTION

1. Technical Field

The present disclosure relates to pulmonary emboli detection and, more specifically, to pulmonary emboli detection with dynamic configuration based on blood contrast level.

2. Discussion of Related Art

A pulmonary embolism (PE) is a blockage, for example a clot, within the arteries that carry blood from the heart to the lungs including the pulmonary artery or one of its branches. Pulmonary emboli can be deadly but may be treated if properly detected. The presence of PEs may be detected with the use of pulmonary angiography. Pulmonary angiography may involve catheterisation of the right atrium of the heart and injection of radiocontrast into the right heart.

Less invasive approaches for the detection of pulmonary emboli have been developed. For example, CT imaging may be used to provide CT pulmonary angiography (CTPA) without the need for injecting radiocontrast directly into the heart. In these approaches, a computer tomography (CT) scanner is used to image the vessel tree and pulmonary arteries of the lungs.

Detection of PEs within the CT images may be performed either manually or automatically. In manual PE detection, a trained medical practitioner, for example a radiologist, manually reviews the CT data to locate evidence of a PE. This practice may be particularly time consuming and tedious as modern CT images contain a vast amount of data.

Moreover, manual reading of the CT image data may be further complicated by various image abnormalities that may look like a PE and may thus lead to a false positive. Examples of such image abnormalities include respiratory motion artifacts, flow-related artifacts, streak artifacts, partial volume artifacts, stair step artifacts, lymph nodes, and vascular bifurcation, among many others.

Upon diagnosis of a PE, an extended course of anti-clotting medications are administered. While treatment may be life-saving to a patient suffering from an actual PE, these medications may lead to bleeding so it is important that misdiagnosis such as false-positive identifications be minimized.

In automatic PE detection, the CT data is analyzed by a computer to detect either a PE or to select regions of suspicion that may be brought to the attention of the radiologist. The radiologist may then pay particular attention to the selected regions of suspicion. Accordingly, automatic PE detection may reduce the amount of time necessary to review CT data for evidence of a PE and may increase accuracy of detection by bringing regions of suspicion, which may have otherwise gone unnoticed, to the attention of the radiologist.

Radio-opaque contrast plays an important role in CTPA. In acquiring CTPA images, the bolus tracking technique is often used to clearly visualize vessels. According to this technique, a bolus of radio-opaque contrast is injected into the patient using a peripheral intravenous cannula. The volume of contrast is then tracked by the CT scanner. CT images are then acquired at a rate fast enough to capture the progress of the contrast moving through the blood vessels.

Image quality may be influenced by the degree to which the radiocontrast mixes with the blood once administered. Several factors such as body weight and injection duration may affect the extent to which proper mixing occurs. While such factors may be controlled for, to some degree, other factors such as the flow rate of the blood can also affect the extent to which proper mixing occurs, and factors such as these may be difficult to control for. Improper mixing of the radiocontrast in the blood may create mixing artifacts in the CTPA images that may result in a suboptimal CTPA study due to non-homogeneous enhancement of blood, as observed by HU values.

Suboptimal CTPA studies may then lead to increased occurrences of false positive PE detection and then perhaps to the needless administration of treatments with serious side effects. On the other hand, suboptimal CTPA studies may lead to increased occurrences of false negatives where patients may not be given potentially life-saving treatments.

SUMMARY

A method for automatically detecting medical anomaly candidates within medical image data using an image processing device includes administering a contrast agent into a patient. A plurality of images is acquired. A level of contrast at a pre-determined anatomic location of the patient is acquired. One or more anomaly candidates are detected based on the determined level of contrast at said pre-determined anatomic location.

A method for automatically detecting pulmonary embolism (PE) candidates within medical image data using an image processing device includes administering radiocontrast into a patient. A sequence of computed tomography (CT) images is acquired. A level of radiocontrast at a pulmonary artery trunk of the patient is determined. One or more PE candidates are detected within a pulmonary artery tree of the patient based on the determined level of radiocontrast at the pulmonary artery trunk. The one or more detected PE candidates are displayed.

The administration of the radiocontrast and acquisition of the sequence of CT images may be performed in a manner consistent with CT pulmonary angiography (CTPA) techniques.

The step of determining the level of radiocontrast at the pulmonary artery trunk may include automatically identifying the pulmonary artery trunk within an image frame of the CT image sequence, locating a point within the automatically identified pulmonary artery trunk, identifying a neighborhood of points around the located point, determining the intensity of each point in the neighborhood of points, selecting a group of the highest intensity points within the neighborhood of points, averaging the intensity of the selected group of highest intensity points, and determining the level of radiocontrast at the pulmonary artery trunk based on the average intensity. The located point may be considered to be part of the neighborhood of points. The neighborhood of points may include the located point and 26 points that are closest to the located point. The group of the highest intensity points within the neighborhood of points may be defined as points among the top 30% of all neighborhood points as determined by intensity values.

The step of detecting one or more PE candidates within the pulmonary artery tree of the patient based on the determined level of radiocontrast at the pulmonary artery trunk may include categorizing the determined level of radiocontrast as falling into one of a plurality of categories, selecting one or more object classifiers associated with the category that the determined level of radiocontrast falls within, and searching for PE candidates using the selected one or more classifiers. The plurality of categories may include a relatively high-contrast category, a relatively low-contrast category, and an inconclusive category. The one or more object classifiers may have been created using a computer learning technique from sets of training data that have been classified according to determined levels of radiocontrast within a pulmonary artery trunk.

The step of detecting one or more PE candidates within the pulmonary artery tree of the patient based on the determined level of radiocontrast at the pulmonary artery trunk may include setting one or more detection parameters according to the determined level of radiocontrast and conducting a search for PE candidates using the set detection parameters.

A method for automatically detecting pulmonary embolism (PE) candidates within medical image data using an image processing device may include receiving training data including a plurality of medical images including pulmonary arteries and one or more identified pulmonary emboli, categorizing the training data according to a determined level of contrast at a pulmonary artery trunk within each medical image, training image classifiers based on each category of training data, and automatically identifying one or more PE candidates from within a subsequent medical image using an image classifier that has been trained with training data for a particular category that corresponds with a level of contrast at a pulmonary artery trunk within the subsequent medical image.

The medical image data may be computed tomography pulmonary angiography (CTPA) image data.

The step of categorizing the training data according to a determined level of contrast at a pulmonary artery trunk within each medical image may includes automatically identifying the pulmonary artery trunk within each image of the training data, locating a point within the automatically identified pulmonary artery trunk, identifying a neighborhood of points around the located point, determining the intensity of each point in the neighborhood of points, selecting a group of the highest intensity points within the neighborhood of points, averaging the intensity of the selected group of highest intensity points and categorizing the training data according to the average intensity.

The step of automatically identifying one or more PE candidates from within a subsequent medical image may include determining the level of contrast at the pulmonary artery trunk within the subsequent medical image, categorizing the determined level of radiocontrast as falling into one of a plurality of categories, selecting one or more object classifiers associated with the category that the determined level of radiocontrast falls within, and searching for PE candidates using the selected one or more classifiers.

The step of determining the level of contrast at the pulmonary artery trunk within the subsequent medical image may include automatically identifying the pulmonary artery trunk within the subsequent medical image, locating a point within the automatically identified pulmonary artery trunk, identifying a neighborhood of points around the located point, determining the intensity of each point in the neighborhood of points, selecting a group of the highest intensity points within the neighborhood of points, averaging the intensity of the selected group of highest intensity points, and categorizing the level of contrast at the pulmonary artery trunk within the subsequent medical image according to the average intensity.

A computer system includes a processor and a program storage device readable by the computer system, embodying a program of instructions executable by the processor to perform method steps for automatically detecting pulmonary embolism (PE) candidates within medical image data. The method includes administering radiocontrast into a patient, acquiring a sequence of medical images, determining a level of contrast at a pulmonary artery trunk of the patient, detecting one or more PE candidates within a pulmonary artery tree of the patient based on the determined level of contrast at the pulmonary artery trunk, and displaying the one or more detected PE candidates.

The step of determining the level of contrast at the pulmonary artery trunk may include automatically identifying the pulmonary artery trunk for an image frame within the sequence of medical images, locating a point within the automatically identified pulmonary artery trunk, identifying a neighborhood of points around the located point, determining the intensity of each point in the neighborhood of points, selecting a group of the highest intensity points within the neighborhood of points, averaging the intensity of the selected group of highest intensity points, and determining the level of contrast at the pulmonary artery trunk based on the average intensity.

The step of detecting one or more PE candidates within the pulmonary artery tree of the patient based on the determined level of contrast at the pulmonary artery trunk may include categorizing the determined level of contrast as falling into one of a plurality of categories, selecting one or more object classifiers associated with the category that the determined level of contrast falls within, and searching for PE candidates using the selected one or more classifiers.

The one or more object classifiers may have been created using a computer learning technique from sets of training data that have been classified according to determined levels of contrast within a pulmonary artery trunk.

The step of detecting one or more PE candidates within the pulmonary artery tree of the patient based on the determined level of contrast at the pulmonary artery trunk may include setting one or more detection parameters according to the determined level of contrast and conducting a search for PE candidates using the set detection parameters.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF THE DRAWINGS

Figure 1:
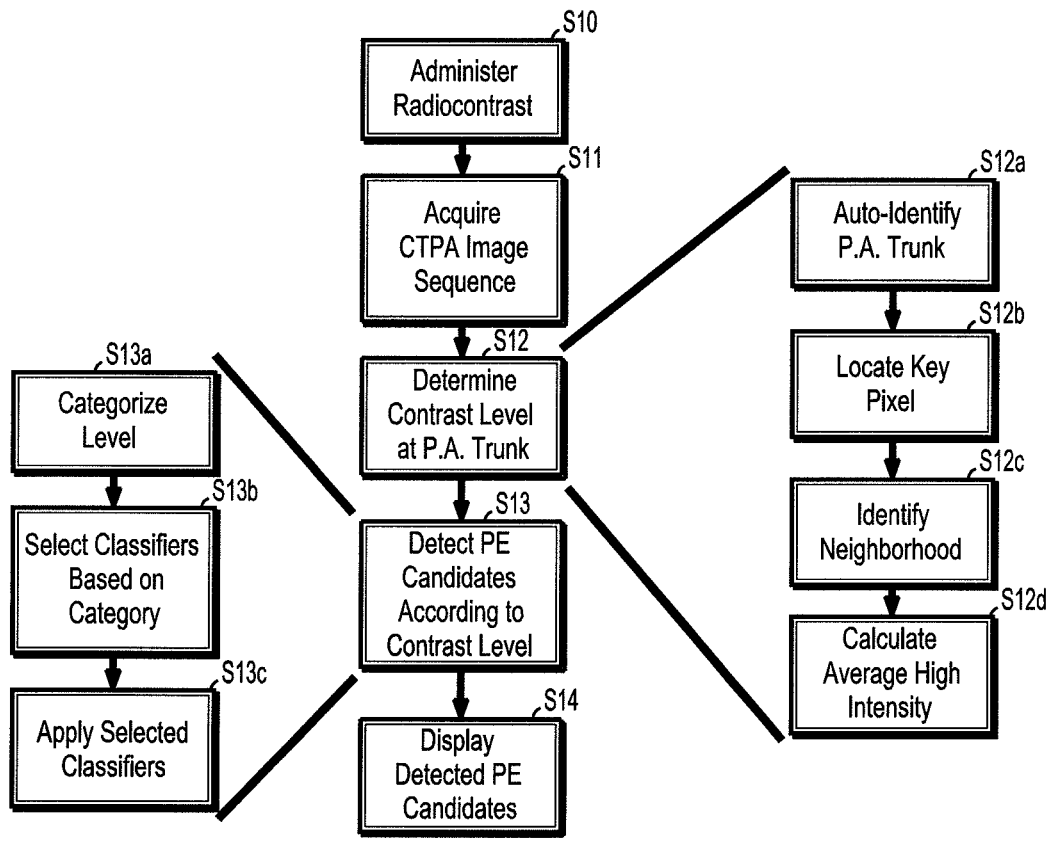
FIG. 1 is a flow chart illustrating an approach for automatic or semiautomatic PE detection according to an exemplary embodiment of the present invention.

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiments of the present invention seek to increase the accuracy and reliability of CTPA studies by automatically correcting for the effects of improper mixing of radiocontrast into the blood thereby minimizing mixing artifacts and potentially reducing false positive and false negative PE detection.

Exemplary embodiments of the present invention may correct for the effects of improper mixing by dynamically configuring CTPA parameters based on a measured concentration of radiocontrast within the pulmonary artery. This measurement may be particularly valuable in assessing the degree of improper mixing because where the blood flow rate is low, a relatively large concentration of radiocontrast may be located in the pulmonary artery, whereas, if the blood flow rate is high, then the radiocontrast passes quickly through the pulmonary artery to reach the portal veins. Accordingly exemplary embodiments of the present invention seek to assess the degree of mixing using measured pulmonary artery contrast level and adapt the CTPA image acquisition accordingly to achieve optimal CTPA studies even where radiocontrast mixing is improper.

Hence, prior to analyzing CT images for finding PE candidates, a level of radiocontrast at the pulmonary artery is assessed. Exemplary embodiments of the present invention set forth various techniques for automatically detecting the radiocontrast level at the pulmonary trunk. FIG. 1 is a flow chart illustrating an approach for automatic or semiautomatic PE detection according to an exemplary embodiment of the present invention. Radiocontrast may be administered (Step S10). Radiocontrast may be administered by injection in accordance with standard CTPA techniques. CT image data may be acquired (Step S11). Acquisition of the CT image data may begin prior to the administration of the radiocontrast, during administration, or shortly thereafter. CT image data may be acquired at periodic intervals, for example, once every second, and may capture the way in which blood flows through the pulmonary arteries forming the vessel tree within the lungs. Accordingly, a CTPA image sequence may be acquired in this step.

The CT image data may then be automatically examined to determine a radiocontrast level at the pulmonary artery trunk (Step S12). The radiocontrast level at the pulmonary artery trunk may be measured, for example, by examining a measure of image intensity such as HU level based on an image slice clearly showing the pulmonary artery trunk, for example, an axial CT slice. The pulmonary artery trunk may be automatically detected within the CT slice using known techniques (Step S12a) and then the image intensity at the automatically detected region may be measured. By detecting the level of radiocontrast present at the pulmonary artery trunk, a likely level of radiocontrast in the pulmonary artery tree inside the lung may be measured and thus PE detection techniques may be tailored to suit the likely level of radiocontrast in the pulmonary artery tree inside the lung.

While many different approaches may be used to determine the level of radiocontrast within the automatically identified pulmonary artery trunk, according to an exemplary embodiment of the present invention, this level may be ascertained by locating a key pixel or other point of the CT slice that represents the pulmonary artery (Step S12b), for example, a central pixel resulting from the automatic identification process used. Then, a neighborhood may be identified (Step S12c), for example, as 26 neighboring pixels to the central pixel. An average intensity may be taken of the most intense pixels from among the neighborhood of pixels (Step S13d). For example, an average value for the highest 30% of pixels by intensity value may be calculated. It is this average value that may then be considered when categorizing CT images as explained in detail below.

Figure 3:
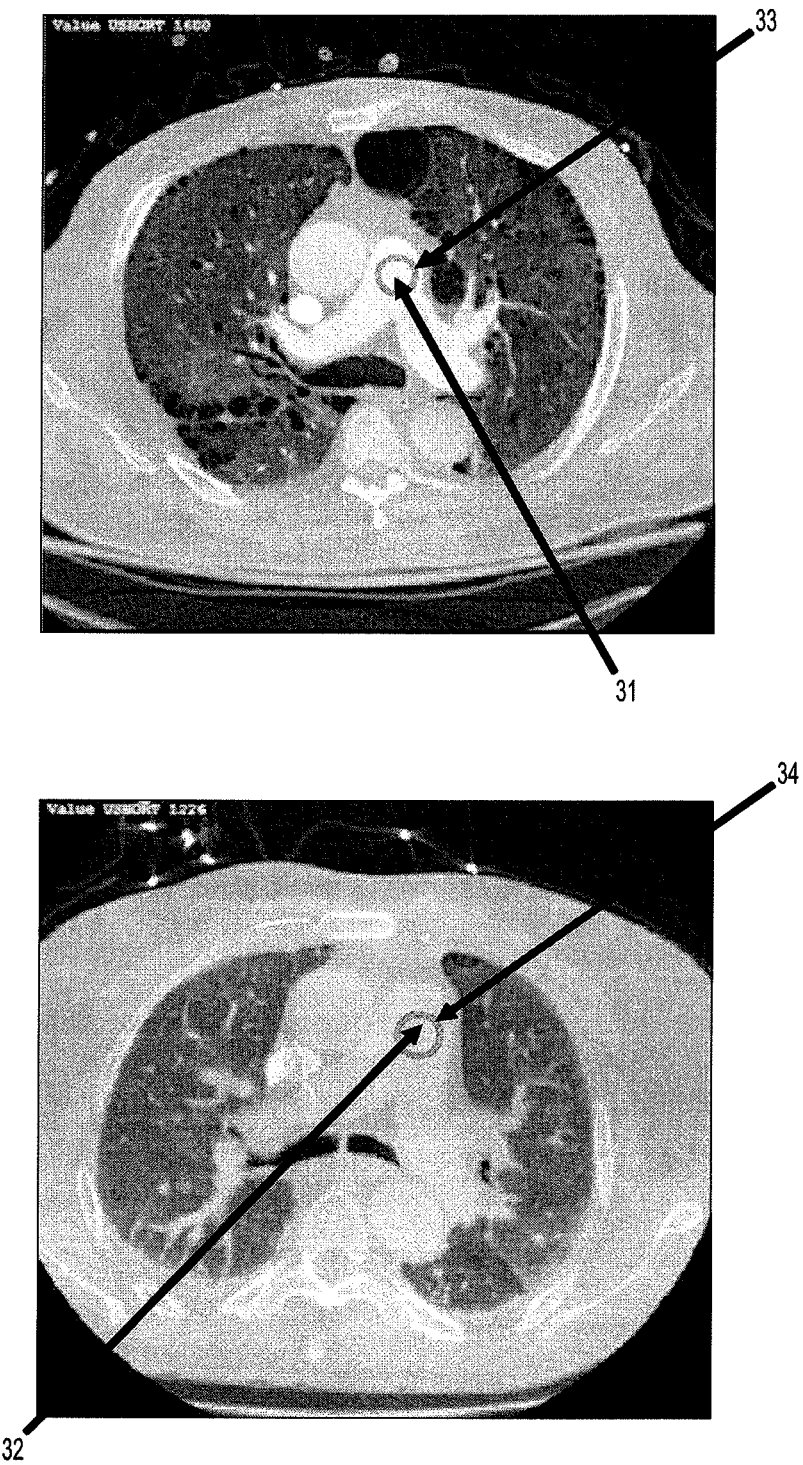
FIG. 3 is a set of sample CT image slices showing a pulmonary artery trunk that has been characterized as having a relatively high level of radiocontrast and a pulmonary artery trunk that has been characterized as having a relatively low level of radiocontrast according to an exemplary embodiment of the present invention.

Probably PE candidates may be detected within the CT image data using one or more detection algorithms, for example, candidate generator (CG) algorithms, the parameters of which have been dynamically configured based on the radiocontrast level at the pulmonary artery trunk (Step S13), for example, as calculated by the average intensity value of most intense pixels within a neighborhood as described in detail above. This may be accomplished, for example, by determining whether the radiocontrast level at the pulmonary artery trunk is relatively high or relatively low. FIG. 3 is a pair of sample CT image slices showing a pulmonary artery trunk that has a relatively high level of radiocontrast (31), here measuring an intensity of 1600 and a pulmonary artery trunk that has a relatively low level of radiocontrast (32), here measuring an intensity of 1226. The circles 33 and 34 represent the automatically detected pulmonary artery trunk.

Thus the CT image may be categorized according to its radiocontrast level at the pulmonary artery (Step S13a). While there may be two categories, for example, a category of relatively high radiocontrast and a category of relatively low radiocontrast, exemplary embodiments of the present invention may utilize more than two categories, for example, three, four or five categories.

Where the CT image is categorized, for example, as having either relatively high or relatively low radiocontrast levels in the pulmonary artery trunk, PE candidate detection techniques may be selected according to the respective category, for example by selecting appropriate shape classifiers (Step S13b). The respective detection techniques may, for example, have been trained using segregated training data that has been similarly categorized, as described in detail below with reference to FIG. 2. The selected PE detection technique may then be applied to the CT image to automatically detect one or more PE candidates.

The determination as to whether the CT image has a high level or low level of radiocontrast within the pulmonary artery trunk may be determined based on a predefined threshold, which may, for example, be measured by pixel intensity levels and compared to the average contrast level, as defined above. According to one exemplary embodiment of the present invention, the CT image may be categorized as high if the average contrast level exceeds 1375 HU and the CT image may be categorized as low if the average contrast level is below 1150 HU. As can be seen from this example, there may be images that are neither high nor low, and they may be categorized, for example, as a middle contrast level having its own classifiers that may be learned either using middle contrast level images or by using the full set of training data.

The detected PE candidates may then be displayed to a user, for example, a radiologist, so that a final diagnosis may be rendered (Step S14). The display may include a rendering of the image data with the one or more PE candidates clearly marked thereon. Alternatively, or additionally, a determination as to whether each of the detected PE candidates is a "true PE" or a "false positive" may be performed automatically using known techniques.

As described above, distinct PE detection techniques and/or classifiers may be utilized for each grouping of CT images. These classifiers may be generated, for example, using computer learning techniques based upon training data. The training data may consist of a set of CT images, each including a slice that shows the pulmonary artery trunk after administration of the radiocontrast, for example, after a predetermined length of time. This slice may be, for example, the axial slice described above. Each set of CT images may also include one or more slices showing the pulmonary artery tree within the lungs including indications of confirmed PEs. These PE indications may have been determined in advance by a trained practitioner, for example, a radiologist and are thus considered part of the training data.

Figure 2:
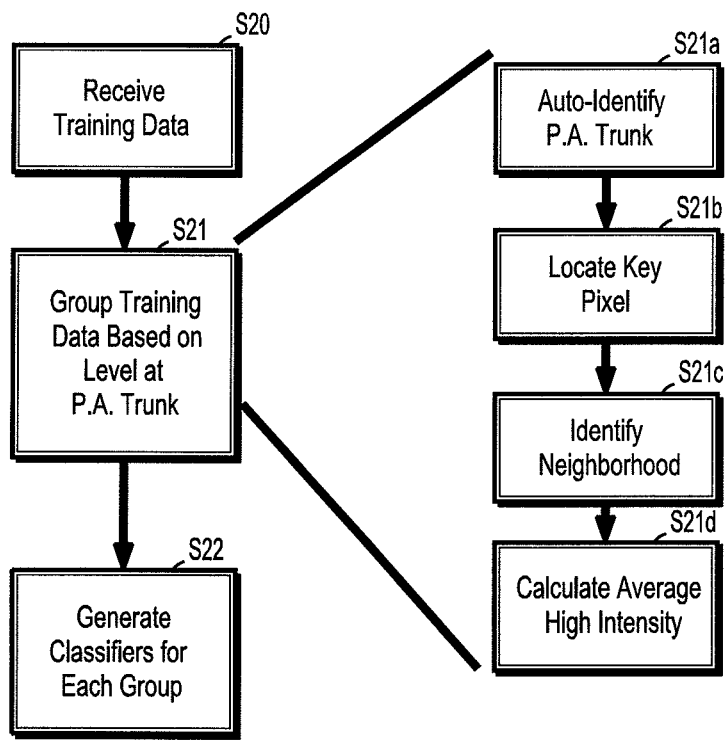
FIG. 2 is a flow chart illustrating an approach for generating distinct PE detection techniques and/or classifiers for various groupings of CT image defined by radiocontrast levels found in the pulmonary artery trunk according to exemplary embodiments of the present invention.

FIG. 2 is a flow chart illustrating an approach for generating distinct PE detection techniques and/or classifiers for various groupings of CT image defined by radiocontrast levels found in the pulmonary artery trunk according to exemplary embodiments of the present invention.

First, the training data may be received (Step S20). The training data may be as described above and may include multiple CT image sets, each including an image slice showing the level of radiocontrast found in the pulmonary artery trunk at the appropriate time as well as one or more slices showing the pulmonary artery tree within the lungs. Each image set may be categorized according to the level of radiocontrast in the trunk of the pulmonary artery (Step S21). This step may include automatically identifying the pulmonary artery trunk (Step 21a), locating a key pixel or point (Step 21b), identifying a neighborhood of pixels (Step S21c), and calculating the average high pixel intensity in the identified neighborhood (Step S21d), each of the steps S21a-d corresponding in large measure to the steps S12a-d described in detail above.

After the training data has been categorized, for example, as either relatively high or relatively low, computer learning techniques may be used to generate classifiers for detecting PEs based on the categorized training data (Step S22). For example, only the training data categorized as high may be used to train the classifiers for detecting PEs in high images and only the training data categorized as low may be used to train the classifiers for detecting PEs in low images. Where there are more than two categories, the training data may be divided accordingly for training purposes.

The categories used to divide training data may be substantially equal to the categories used to categorize the CT image for the purposes of PE detection, as described above. Alternatively, the categories used to divide the training data may be somewhat different. For example, the categories used for the purposes of PE detection may be either high, low, or indeterminate, wherein the high category is defined as above a high threshold, the low category is defined below a low threshold and the indeterminate category is defined as between the high and low threshold. Yet for the purposes of training, the training data may be divided into high and low groupings by a single threshold that is defined as halfway between the high and low thresholds. Then three groupings of classifiers may be trained including a high group, a low group and a total group including the high and low group. Then in PE detection, PE candidates are detected in high images using the high classifiers, PE candidates are detected in low images using the low classifiers, and PE candidates are detected in indeterminate images using the classifiers of the total group. In this way, PE candidates are identified in CT images that do not clearly have a high radiocontrast level in the pulmonary artery trunk and do not clearly have a low radiocontrast level in the pulmonary artery trunk using general purpose PE detection classifiers.

After the classifiers have been generated for each group, the generated classifiers may be used to detect PE candidates, for example using the approach discussed above with respect to FIG. 1.

Figure 4:
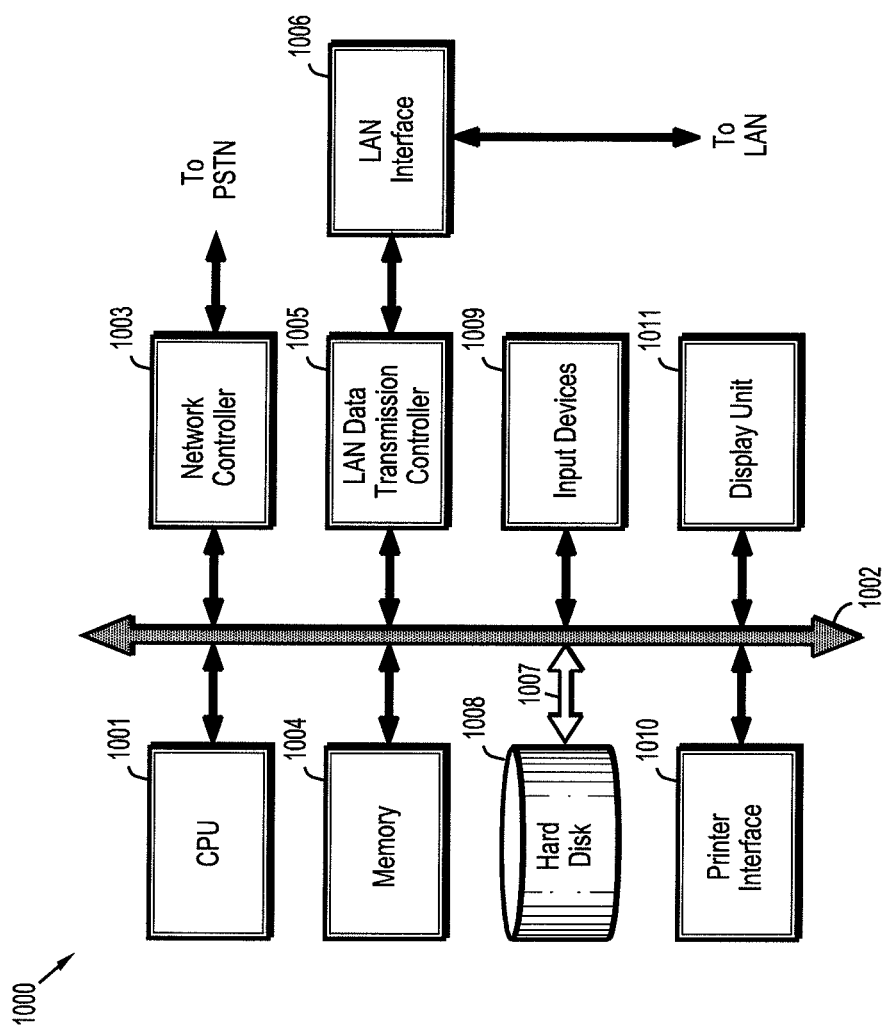
FIG. 4 shows an example of a computer system capable of implementing the method and apparatus according to embodiments of the present disclosure.

FIG. 4 shows an example of a computer system which may implement a method and system of the present disclosure. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk, 1008 via a link 1007.

While the description talks about CT, exemplary embodiments of the present invention may also be applicable to other modalities, for example, magnetic resonance imaging (MRI), positron emission tomography (PET), etc. While the description talks about pulmonary embolism, exemplary embodiments of the present invention may also be applicable to other medical anomalies like breast tumors, etc. While the description talks about classifiers, other methods like neural nets, etc could also be used.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A method for automatically detecting pulmonary embolism candidates within medical image data using an image processing device, comprising:

administering a contrast agent into a patient;
acquiring a plurality of images;
automatically determining by the image processing device a level of contrast agent at a pre-determined anatomic location of the patient, wherein the pre-determined location is the pulmonary artery trunk, comprising:
  automatically identifying by the image processing device the pre-determined anatomic location within an image frame of the plurality of images;
  locating by the image processing device a point within the automatically identified pre-determined anatomic location;
  identifying by the image processing device a neighborhood of points around the located point;
  determining by the image processing device the intensity of each point in the neighborhood of points;
  selecting by the image processing device a group of the high intensity points within the neighborhood of points;

averaging by the image processing device the intensity of the selected group of high intensity points; and determining by the image processing device the level of radiocontrast agent at the pulmonary artery trunk based on the average intensity; and detecting by the image processing device one or more pulmonary embolism candidates based on the determined level of contrast agent at the pulmonary artery trunk.

2. The method of claim 1, wherein
the medical image data is a sequence of computed tomography data (CT).

3. The method of claim 1, additionally comprising the step of displaying the one or more pulmonary embolism candidates.

4. The method of claim 1, wherein the administration of the contrast agent and acquisition of the plurality of images is performed in a manner consistent with CT pulmonary angiography (CTPA) techniques.

5. The method of claim 1, wherein the located point is considered part of the neighborhood of points.

6. The method of claim 5, wherein the neighborhood of points includes the located point and 26 points that are closest to the located point.

7. The method of claim 1, wherein the group of the highest intensity points within the neighborhood of points is defined as points among the top 30% of all neighborhood points as determined by intensity values.

8. The method of claim 1, wherein the step of detecting one or more pulmonary embolism candidates at the pre-determined anatomic location based on the determined level of contrast agent at the pre-determined anatomic location:

categorizing the determined level of contrast agent as falling into one of a plurality of categories;

selecting one or more object classifiers associated with the category that the determined level of contrast agent falls within; and searching for anomaly candidates using the selected one or more classifiers.

9. The method of claim 8, wherein the plurality of categories include a relatively high-contrast category, a relatively low-contrast category, and an inconclusive category.

10. The method of claim 8, wherein the one or more object classifiers were created using a computer learning technique from sets of training data that have been classified according to determined levels of contrast agent within the pre-determined anatomic location.

11. The method of claim 1, wherein the step of detecting one or more pulmonary embolism candidates within the pre-determined anatomic location of the patient based on the determined level of contrast agent at the pre-determined anatomic location includes setting one or more detection parameters according to the determined level of contrast agent and conducting a search for anomaly candidates using the set detection parameters.

12. The method of claim 1, wherein the step of detecting one or more pulmonary embolism candidates includes utilizing a candidate generator algorithm to detect the one or more pulmonary embolism candidates, the parameters of which have been dynamically configured based on the determined level of contrast agent at the pre-determined anatomic location.

* * * * *